United States Patent
Echols

(10) Patent No.: US 12,357,710 B2
(45) Date of Patent: Jul. 15, 2025

(54) RADIOPAQUE CONTRAST AGENT

(71) Applicant: Scarlet Imaging, LLC, Salt Lake City, UT (US)

(72) Inventor: Michael Scott Echols, Salt Lake City, UT (US)

(73) Assignee: SICREATIONS, LLC, Salt Lake City, UT (US)

(*) Notice: Subject to any disclaimer, the term of this patent is extended or adjusted under 35 U.S.C. 154(b) by 523 days.

(21) Appl. No.: 14/836,717

(22) Filed: Aug. 26, 2015

(65) Prior Publication Data

US 2016/0030601 A1 Feb. 4, 2016

Related U.S. Application Data

(63) Continuation-in-part of application No. 14/446,111, filed on Jul. 29, 2014, now abandoned.

(51) Int. Cl.
*A61K 49/04* (2006.01)

(52) U.S. Cl.
CPC ...... *A61K 49/0404* (2013.01); *A61K 49/0419* (2013.01)

(58) Field of Classification Search
CPC ............ A61K 49/0419; A61K 49/0404; A61K 49/0414
See application file for complete search history.

(56) References Cited

U.S. PATENT DOCUMENTS

| | | | | |
|---|---|---|---|---|
| 3,212,973 | A | 10/1965 | Roberts et al. | 424/9.4 |
| 3,419,657 | A | 12/1968 | Sanders | 424/9.45 |
| 4,215,103 | A * | 7/1980 | Millington | A61K 49/0404 222/146.6 |
| 4,729,897 | A | 3/1988 | Poppe et al. | 426/96 |
| 6,113,629 | A | 9/2000 | Ken | 623/1.1 |
| 8,467,493 | B2 | 6/2013 | Purchio et al. | |
| 2010/0063174 | A1 * | 3/2010 | Ruberti | C08J 3/075 523/113 |
| 2010/0183212 | A1 | 7/2010 | Purchio et al. | |

OTHER PUBLICATIONS

Bergeron et al., Plastic and Reconstructive Surgery, 2006, 117, p. 2051-7.*
Helminger et al., Adv. Funct. Mater., 2014, 24, p. 3187-3196.*
Lister et al., Arch. Dis. Childh., 1964, 39, p. 131.*
Carr, J. Bone and Joint Surgery, 1988, 70-B, p. 319-321.*
Hales, Yale Journal of Biology and Medicine, 1971, p. 257.*
Garter et al., J. Reprod. Fert., 1971, 25, p. 201-10. (Year: 1971).*
"Exsanguanate", https://www.dictionary.com/browse/exsanguinate, Mar. 1, 2020 (Year: 2020).*
Langheinrich et al., Radiology, 2004, 233, p. 165-171. (Year: 2004).*
The Physics Factbook, 2001, https://hypertextbook.com/facts/1998/LanNaLee.shtml (Year: 2001).*
Thebaud et al., Circulation, 2005, p. 2477-2484. (Year: 2005).*
Bristol et al., Veterinary Radiol., 1991, 32(4), p. 196-205.
Saunders, Nature, 1957, 4598, p. 1353.
Saphier et al., Int. J. Pharm., 2010, 388(1-2), p. 190-5.
Morris et al., Cir. Plas. Iberolatinoam., 2006, 32(4), p. 225-36.
Vivien Marx, Molecular Imaging, C&EN Northeast News Bureau, Jul. 25, 2005, p. 25-34, vol. 83, No. 30.
Silke Grabherr, Marco Dominietto, Lisa Yu, Valentin Djonov, Bert Muller, Sebastian Friess, Angiofil: a novel radio-contrast agent for post-mortem micro-angiography, 2008, vol. 7078.
Eric D. Agdeppa, Mary E. Spilker, A Review of Imaging Agent Development, The AAPS Journal, Jun. 2009, vol. 2.
Daniel L. Small, David Weinstein, Christine O'Day, Glenn Knitter, Naveen Oullette, Liane Pinkos, Sergio X. Vasquez, Neha Shah, AltaBlu Prime and Microfil 3D Imaging of Tumor Vasculature, Numira Biosciences.
Contrast Agents for ex Vivo an in Vivo Imaging, Article About Contrast Agents, 2007.
Chittenden, R.H. and Solley, Fred P., "The Primary Cleavage Products Formed in the Digestion of Gelatin", J Physiol., April 1891, pp. 23-33, vol. 12, Issue 1; https://www.ncbi.nlm.nih.gov/pmc/articles/PMC1514214/.
Ganji, Fariba et al., "Theoretical Description of Hydrogel Swelling: A Review", Iranian Polymer Journal (2010), pp. 375-398, vol. 19, Issue 5; http://journal.ippi.ac.ir.

* cited by examiner

*Primary Examiner* — Michael G. Hartley
*Assistant Examiner* — Leah H Schlientz
(74) *Attorney, Agent, or Firm* — MaxGoLaw PLLC

(57) ABSTRACT

A radiopaque composition is provided that includes an inorganic opacifying agent distributed through an aqueous gelatinous substance in an aqueous solvent. A process for making a radiodense vascular fill composition includes adding a gelatinous substance to an aqueous solution. An inorganic opacifying agent suspension is formed in a saline solution or water. The inorganic opacifying agent and gelatin are mixed with water or saline. A process of imaging a vascular system of a subject includes placing a subject under anesthesia or sedation and exsanguinating the subject. An isotonic fluid is then flushed through the vascular system and the radiopaque composition is infused into the subject circulatory system at a temperature of 40 degrees Celsius or greater. After waiting a given time interval for the radiopaque composition to cool and form a solid gel, an imaging scan is performed on the subject.

18 Claims, 2 Drawing Sheets

RADIOPAQUE CONTRAST AGENT

CROSS-REFERENCE TO RELATED APPLICATION

This application is a continuation in part of U.S. patent application Ser. No. 14/446,111 filed Jul. 29, 2014, which is incorporated herein by reference.

FIELD OF THE INVENTION

The present invention in general relates to the field of imaging and in particular to an improved composition and process for imaging an entire vascularized organism and some tubule based mechanical systems.

BACKGROUND OF THE INVENTION

Radiodensity or synonymously, radiopacity refers to the relative inability of electromagnetic radiation, particularly X-rays, to pass through a particular material. Radiolucency refers to transparency or "transradiancy" to X-ray photons. Materials that inhibit the passage of electromagnetic radiation are commonly referred to as radiodense, while those that allow radiation to pass more freely are commonly referred to as radiolucent. The term refers to the relatively opaque white appearance of dense materials or substances on radiographic imaging studies, compared with the relatively darker appearance of less dense materials.

Medicine and veterinary science have been revolutionized by radiographic imaging using radiodense contrast media that can be passed through the bloodstream, the gastrointestinal tract, or into the cerebral spinal fluid in the context of computed tomography (CT) scan or X-ray imaging. The fields of general and bioengineering have also use contrast radiography to evaluate patency of select tubular parts of mechanical systems. The resulting imagery has highly accurate and detailed anatomic and physiologic images of the body or mechanical system that are not compromised, as was common with dissection or artistic renderings of features.

Conventionally, CT is optimal in terms of speed and resolution for visualizing the skeletal system, whereas MRI offers unparalleled soft-tissue contrast (e.g., gray and white matter in the brain). Apart from the lyophilic colloids, such as barium sulfate, iodine compounds are commonly used because of the high x-ray absorption cross-section associated with iodine. An effective but time-consuming alternative is the filling of vessels or cavities with resins, such as methyl methacrylate. After resin polymerization, the tissue can be dissolved and a fragile construct formed of the polymerized resin that can be easily imaged. By using either exogenous or endogenous contrast agents, additional information of the body can be captured. For example, images of the vascular system (i.e., angiography) can be obtained via the so-called contrast-enhanced digital subtraction CT or time-of-flight MRI. The detailed morphological analysis of the vascular tree allows for assessing the basic anatomy, physiological conditions and metabolic functions of the subject specimen. As advances in genetics have made animal models of human disease available, there has been an increase in the types of equipment and technologies dedicated to small animal imaging, with a distinct emphasis on murine models.

Accurate anatomy references and commonly recognized nomenclature serve as a foundation for understanding of health and disease in all species, and are critical for clinical evaluation and scientific study, communication and education. These basic tenets are long accepted and have resulted in numerous anatomy resources, with commonly accepted nomenclature, available for humans, dogs, cats and a few other mammalian species.

However, when working with small animal species, including rodents, birds, reptiles and more, currently available contrast agents have proven to provide less than satisfactory results for imaging the whole body cardiovascular system. Furthermore, the skeletal anatomy of birds and other small animals is hard to capture because of the low mineral density. X-ray radiography and CT scans of captive birds often yield suboptimal results. Commonly available intravenous contrast dyes include iodine based, experimental intravenous agents (nanoparticle suspensions), and new magnetic resonance imaging (MRI) 'time of flight' procedures have all been employed with unsatisfactory results.

A commonly used intravenous product called MICROFIL® (silicon rubber) has also yielded unsatisfactory results. MICROFIL® compounds are radiopaque polymers that fill and opacify the vasculature of non-surviving animals when perfused through the heart or specific vessels at the time of sacrifice. Following injection, MICROFIL® compounds cure to form a three-dimensional cast of the vasculature. MICROFIL® is currently considered the state of the art in vascular imaging, however the material is difficult to work with, has a limited open working time, and is a poor performer when perfusing an entire animal, creating multiple filling voids that result in poor vascular maps when viewed with micro computerized tomography (CT). However, MICROFIL® is commonly used to perfuse single organs requiring cannulation of specific (usually surgically exposed) vessels.

In work conducted in a study by Bristol et al. as detailed in a paper entitled "Use of a Barium/Gelatin Mixture to Study Equine Vasculature with Potential Application in Free-Flap Transfer" that appeared in *Veterinary Radiology*, Vol. 32, No. 4, 1991, pp 196-205, a vascular radiopaque contrast dye based on a contrast medium solution with 30% weight by volume of barium sulfate and 4% weight by volume of gelatin, where the solution that was kept at 37° C. met with limited success in vascular imaging. As Bristol et al. state on pages 198-199, "venous anatomy was difficult to determine because of the poor filling with contrast medium". Additionally on page 202, Bristol et al. state "The radiographs obtained after perfusion of intact animals by this method were satisfactory for study of cutaneous vasculature.", however on page 202 Bristol et al further state that "Deeper, larger veins were often difficult to identify due to poor filling with contrast medium."

By accurately defining the vascular system, one can reconstruct soft tissues not easily readily visible using current technology including organs, cartilage, nerves, neoplasias, granulomas and more. Additionally, a clear understanding of the vascular supply helps better define certain bony structures (for example foramina, growth plates, healing injuries and more) not evident without angiography.

Thus, there exists a need for an improved vascular radiopaque contrast dye that can improve on the image quality of a vascular, skeletal and soft tissue system of an entire organism, as compared to existing dyes and techniques. There also exists a need for such contrast dyes tailored to provide entire body vascular contrast for mammalia, avian, amphibian, reptilian, fish and plant species. The same is true of human autopsy samples. There further exists a need for such a contrast dye that provides comparable full-body vascular contrast in murine and rodent models to promote cross-species comparisons.

SUMMARY OF THE INVENTION

A radiopaque composition is provided that includes an inorganic opacifying agent distributed through an aqueous gelatinous substance in an aqueous solvent. In specific embodiments, the inorganic opacifying agent is present from 10-25 percent weight by volume (w/v) and gelatin is present in an amount of between 5-20 percent weight by volume (w/v) as the aqueous gelatinous substance.

A process for making a radiodense vascular fill composition includes adding a gelatinous substance to water or a saline solution. A gelatinous substance is added and with stirring and heating, a gelatin solution is created at a temperature of 60 degrees Celsius or greater. An inorganic opacifying agent is dispersed in the gelatin solution to form the radiodense vascular fill composition. The radiodense vascular fill composition is maintained at a temperature of 60 degrees Celsius or greater. Alternatively, dry inorganic opacifying agent and gelatin are stored in a premixed capsule, separate capsules or other container and then added to and mixed with water or saline and heated with stirring to form the radiodense vascular fill composition.

A process of imaging a vascular system of a subject includes placing a subject under anesthesia or sedation and then placing and securing a first intravenous (IV) catheter and a second IV catheter at opposite ends of a vessel in the body of the subject. Alternatively, the second (distant) vessel or limb can be severed to allow for blood drainage or other technique employed to exsanguinate the subject. An isotonic fluid with or without heparin or other anticoagulant and/or vasodilator is/are then flushed through the vascular system and the radiopaque composition is infused into the first IV catheter at a temperature of 60 degrees Celsius or greater. After waiting a given time interval for the radiopaque composition to cool and form a solid gel, an imaging scan is performed on the subject. Alternatively an anticoagulant and/or vasodilator can be administered to the subject prior to flushing with isotonic fluids.

BRIEF DESCRIPTION OF THE DRAWINGS

The present invention is further detailed with respect to the following drawings. These figures are not intended to limit the scope of the present invention but rather illustrate certain attributes thereof.

DESCRIPTION OF THE INVENTION

Figure 1:
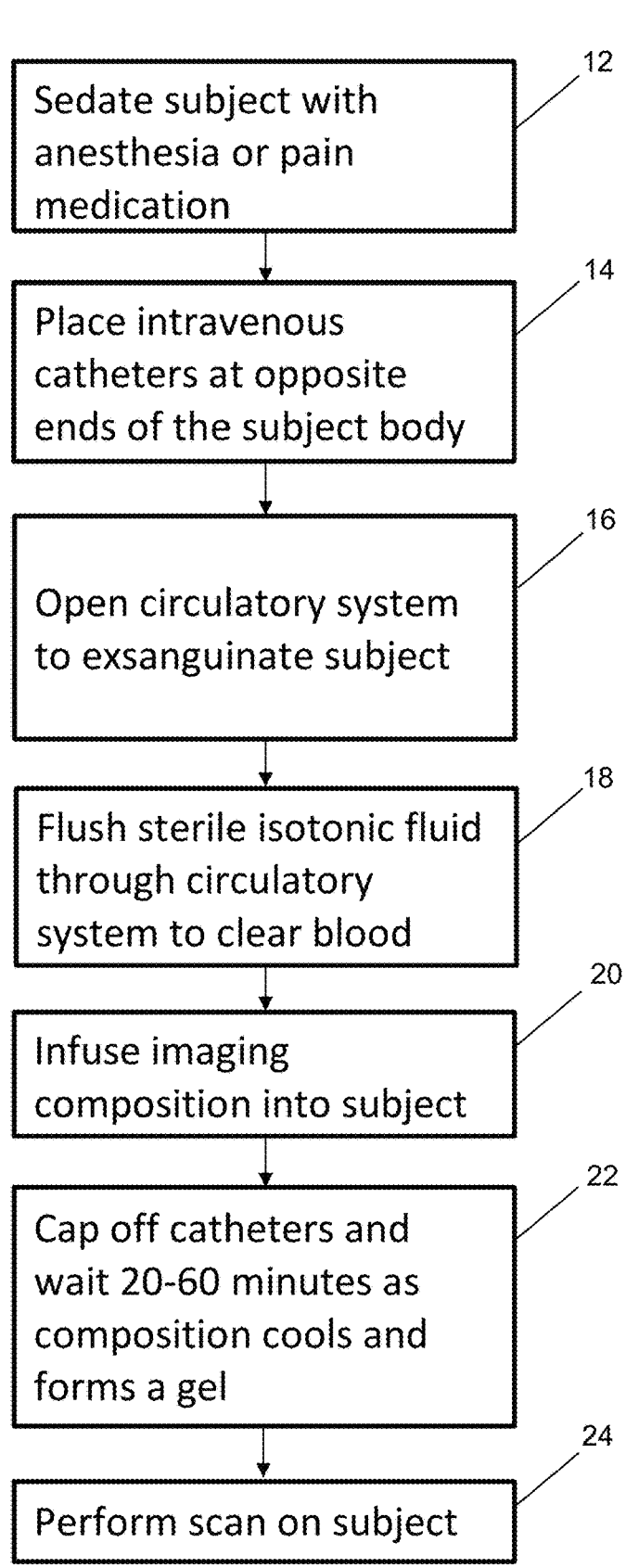
FIG. 1 is a flowchart of a method of using the imaging composition in a subject according to embodiments of the invention.

The present invention has utility as an intravenous radiopaque composition that can image a vascular system of an entire animal, especially for birds, reptiles, amphibians, fish, vascular plants, small mammals, deceased humans, and mechanical devices with a tubular structure. The present invention affords advances to fields illustratively including anatomy, drug discovery, embryology, toxicology, and plant breeding. Embodiments of the inventive radiopaque composition achieve highlighting fill of the vascular system of a non-human subject using low cost, relatively non-toxic and easy to administer materials that can be readily imaged using computed tomography (CT) or standard radiograph techniques.

In certain inventive embodiments, with radiopaque substance having a size of less than 40 microns, vessels in a subject with an inner diameter as small as 100 microns are readily filled, while in other embodiments, vessels with an inner diameter as small as 40 microns are filled. As used herein, a radiopaque substance and an opacifying agent are used synonymously. Embodiments of the composition are utilized in an inventive process to perfuse an entire non-human subject vascular system; in contrast to prior art compositions, such as MICROFIL®, that results in filling voids. In certain embodiments of the present invention, the composition flows through the subject vascular system without clogging vessels. In still other inventive embodiments an inventive composition flows through and fills capillaries. It is appreciated that the CT slice thickness and resolution determine the size and detail of the vessels visualized. According to the present invention, scanning can begin immediately after perfusion with an embodiment inventive composition is complete, or alternatively, perfused tissues can be harvested and stored in formalin for later scanning By adding visual light spectrum or fluorescent dye to the inventive contrast agent composition, visualization of vasculature is improved during gross dissection, as compared to an inventive composition lacking such a dye.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

An inventive composition in prototypical form is a mixture of an opacifying agent, an aqueous gelatinous substance, and in some inventive embodiments, a physiologically isotonic buffer in lieu of water or buffers of differing molality (hypo-tonic or hyper-tonic). Buffers operative herein illustratively include saline, phosphate, and combinations thereof. In other inventive embodiments, a water miscible co-solvent of formalin, $C_1$-$C_4$ alkyl alcohol, acetone, phenol, or a combination thereof is provided to form an aqueous solvent system. It is appreciated that a co-solvent can provide attributes illustratively including improved tissue preservation, greater organic dye solubility; as compared to a purely aqueous solution.

As used herein, "isotonic" refers to a solution or composition that is within 10% of the osmality of the subject venous blood in units of osmoles per liter (Osm/L). As used herein non-isotonic solution refers to a solution beyond isotonic osmality and is either hypo-tonic or hyper-tonic.

Opacifying agents operative herein are inorganic and illustratively include barium based compounds illustratively including barium sulfate, and barium titanate; inorganic iodine; aluminum metal, aluminum based compounds illustratively including aluminum trihydroxide, and aluminum oxide; bismuth metal, bismuth based compounds illustratively including bismuth iodide; silver metal, and silver based compounds illustratively including silver nitrate, silver chloride and silver phosphine ligand compounds; lithium metal, and lithium based compounds illustratively including lithium carbonate; gold metal, and gold based compounds illustratively including gold salt complexes and gold phosphine ligand compounds, copper metal, and copper based compounds illustratively including copper phosphine ligand compounds, zinc metal, and zinc based compounds illustratively including zinc oxide and zinc sulfate; platinum metal, and platinum based compounds; iron metal, and iron based compounds illustratively including iron oxides and iron sulfides, stainless steel; or combinations thereof. The opacifying agent having an average domain size of 40 microns or less, while being detectable by MRI, CT scan machines. While a dispersed particulate opacifying agent is always present, in some inventive embodiments the aqueous solution or aqueous solvent system also includes a water soluble metal salt as a secondary opacifying agent. In preferred embodiments of the present invention, the opacifying agent and any secondary soluble opacifying agents are selected to be non-toxic (exclude lead and uranium) to facilitate environmental cremation or burial of the subject. In a specific embodiment, the opacifying agent has a median particle size of 5 nanometers to 15 microns. It is appreciated that inorganic opacifying agents are readily formed in the size range of 5 to 1000 nanometers through conventional techniques illustratively including metathesis reactions in inverse micelles, or in the presence of a chelating agent that functions to terminate crystal growth. With surface area increasing as the inverse of particle radius, such small particles with a size of 5 to 1000 nanometers have the attributes of longer settling times, higher viscosity and improved vascular penetration/adhesion; as compared to larger particles of the same opacifying agent.

A gelatinous substance operative herein is illustratively gelatin; agar; agarose; another polysaccharide polymer material such as pectin, carrageenans, or alginates; methyl cellulose gel; or a combination thereof. In certain inventive embodiments, the gelatinous substance is gelatin. With respect to the properties of gelatin, gelatin is defined as laboratory grade derived from bovine, porcine or other animals hide, hair, hooves, bone or other tissues. In certain inventive embodiments, the gelatin has the attributes of 100-350 bloom and −5 to +40 SGN mesh particle sizes.

In specific inventive embodiments it has surprisingly been found that concentrations of gelatin in the range of 5 to 20 percent weight by volume (w/v) provide an optimal viscosity to suspend opacifying agents in solution. In a specific embodiment a solution with 10-25 percent w/v of opacifying agent and 7-20 percent w/v of gelatin have been shown to be effective to image the arteriovenous anatomy of a subject. In the following examples, the opacifying agent is barium sulfate present in the range of 10 to 25 percent w/v. It has also been found that concentrations of less than 5 percent w/v of gelatin has proven to be insufficient to effectively suspend opacifying agent particulate such as 1 micron diameter barium sulfate, with the particulate settling out of the gelatin solution and thereby causing non-uniform distributions of the opacifying agent in the regions to be scanned. It has also been found that maintaining the opacifying agent composition including gelatin in a temperature range of at least 45 Celsius provides a sufficient viscosity to successfully perfuse and later image the arteriovenous anatomy of the subject.

It is noted that in order to achieve 'satisfactory' cutaneous vascular filling the solution should not become viscous or begin to gel at the time of perfusion. It is important to heat the gel up to a point where a gelatinous solution is a free flowing solution. No matter how much pressure is put on a perfusion system, once viscosity increases and gelling occurs, the capillaries quickly become occluded. Increased pressure will either result in vascular rupture or perfusion along the path of least resistance (large vessels and most likely primarily arteries).

In a specific embodiment, the gelatinous solution is heated with stirring to at least 60 Celsius (and in certain embodiments to a range of 80-90 Celsius) and perfusion is conducted at temperatures above 40 Celsius. It is appreciated that with addition of volatilized solvent and stirring, an inventive composition can be maintained at elevated temperature for more than an hour or even for several days. The higher preparation temperature acts to weaken and slow the gelling process making for a more fluid solution. The higher perfusion temperature delays the onset of increasing viscosity and gelling, thereby allowing the formulation to penetrate capillaries and fill the veins and not just arteries.

With respect to the properties of agar, agar is defined as laboratory grade derived from *Gelidiella acerosa*. With respect to the properties of agarose, agarose is defined as laboratory grade derived from generally extracted from *Gelidium* algae and having a melting temperature 34-38 Celsius.

It is appreciated that a gelatinous substance having a gelling temperature in solution that is greater than or equal to the core temperature of the subject is particularly well suited to disperse through the vascular system of a given subject. An attribute of a gelatinous substance in solution is that it can be maintained at a temperature of between 45 and 60 Celsius for several hours upon provision for water loss.

An attribute of an inventive composition is reduced toxicity compared to conventional products that use more toxic, expensive and complex ingredients. Additionally, it is noted that the through the present invention controlling osmality and being aqueous in nature, that vasculature being imaged remains representative of that in living physiology; and inhibits vascular edema associated with conventional agents.

It is appreciated that a storage stable powder is provided containing appropriate proportions of the opacifying agent and the gelatinous substance that only requires addition of water and solutes, isotonic solution, non-isotonic solutions, or an aqueous solvent system inclusive of a co-solvent to form an inventive imaging composition.

Referring now to the figures, FIG. 1 is a flowchart of a process 10 for introducing an embodiment of the inventive radiopaque contrast dye to the vascular system of a subject. With the animal under anesthesia or heavily sedated with pain medication (Block 12), two intravenous (IV) catheters are placed at opposite ends of the subject body (Block 14), and the animal is exsanguinated (Block 16). Ideally, one catheter carrying the inventive radiopaque contrast dye solution is directed towards the heart (in the normal direction of venous flow), while the other catheter is directed away from the heart. It is appreciated that other catheter configurations are operative herein such as for example when both catheters are placed towards the heart. Alternatively, the same vein or vessel is used with one catheter placed in the direction of the heart and one away from the heart. The section of vessel between the two catheters is ligated and completely occluded. The two catheters are securely sutured in place to inhibit leakage. In an alternative inventive embodiment, one intravenous catheter is placed and a separate distant vessel is dissected from beneath the skin and either nicked (to allow for leakage) or ligated proximally (on the side towards the heart) and cut to allow drainage out the body. In an alternative inventive embodiment, one intravenous catheter is placed and a distant limb (foot, tail, etc.) is severed to allow for blood drainage.

Once the catheters are in place, a flush (Block 18) is provided using sterile isotonic (normal body composition) fluids (such as 0.9% NaCl, 2.5% Dextrose, Lactated Ringers Solution, Normosol, etc.) with or without heparin (1:1000 U/ml) at 0.5-5 cc per 100 cc of isotonic fluids into the catheter directed towards the heart. It is noted that heparin may be added prior to administration of exsanguination fluid. While flushing the isotonic fluids, blood should come out the opposite IV (or nick incision or severed) site. It is appreciated that flushing is also readily accomplished with distilled water, tap water, hypertonic solutions, or hypotonic solutions in lieu of the isotonic solution. In still other inventive embodiments where tissue preservation is desired, flushing readily occurs with a formalin solution or phenol solution. Formalin or phenol acts as a preservative and offers an option to preserve the specimen during perfusion. Generally, 20-60 total weight percent of the subject body weight worth of fluids is flushed. A qualitative flush amount includes sufficient fluid being introduced into the subject to produce clear to weak blood tinged fluid exiting the opposite IV or nick incision/severed site. It is appreciated that infusion pressures of the fluid are dependent on the size and type of subject. Infusions may be hand delivered via a syringe, or via an introducing machine. It is noted that an intra-osseous catheter is also used to deliver the solution for some animals.

Once the blood has been adequately flushed from the body, the opacifying agent-gelatinous mixture (Block 20) is introduced into the IV catheter directed towards the heart at a temperature of between 30 and 90 degrees Celsius. The mixture is continually infused until exiting the opposite catheter or nick/severed site as (visibly) concentrated as it is going in. Once the body has been judged adequately perfused, the catheter(s) is (are) capped (Block 22) or the nick/amputation site is lightly covered with a bandage to prevent further leakage. Within 20-60 minutes, the solution has cooled and should not leak as it forms a solid gel. The whole animal subject or harvested portions are then imaged using CT, radiography, MRI, or other imaging modalities (Block 24). Imaging can begin immediately after infusion once all leakage has stopped. Harvested tissue can also be immediately scanned or soaked in standard fashion in formalin, glutaraldehyde, or other fixative(s) and/or preservative(s) for later scanning and/or traditional histological staining for later scanning and or traditional histological staining.

Embodiments of the inventive composition allow for creation of gross and digital (with the aid of CT/radiography) vessel visualization for anatomy study. Study may include classroom up to research study. 'Study' includes anything where the anatomy of the study subject needs to be understood. Vascular anatomy knowledge gives one shape and size of organs, shunts and other vascular anomalies, tumors, and other tissues. This information is vital to understanding basic anatomy, biology and behavior of tissues.

Subjects infused with an inventive radiopaque composition may be used to create digital images that are used to help develop other imaging products and studies. For example, performing MRI time of flight on selected animals is conducted first, and then following up with the contrast product injection and CT. The contrast CT images may be used as the gold standard to help in understanding what is being seen on the time of flight study (non-invasive means to look at blood vessels). In other words, a match between the two images (CT and MRI) can be made, and information from the contrast CT may be used to improve upon the time of flight procedure. The same can be true with developing other imaging processes where an accurate vascular map (as created with embodiments of the inventive imaging composition) is needed for comparison.

EXAMPLES

Example 1

Figure 2:
FIG. 2 is a CT scan of a grey parrot head imaged with the composition and process of an embodiment of the invention.

A formulation of the radiopaque composition as a mixture of barium sulfate, gelatin, water and saline as follows: 1. 7.2 g unflavored gelatin added to 80 cc $H_2O$ at 100 Celsius. Use a hot plate and inert stirring rod to dissolve the gelatin and put gelatin in solution with no visible solid material with stirring at a temperature of between 45 and 60 degrees Celsius.
  2. 80 cc 3:1 60% weight by volume (w/v) Barium sulfate as an opacifying agent: 0.9% saline (NaCl).
  3. Mix the barium sulfate mixture (step 2) into the dissolved gelatin (step 1) while the inert stirring rod stirs the mixture.
  4. Alternatively, food coloring can be added (generally 0.5-2.0 cc per 160 cc of the combination described above). Alternatively, fluorescent or other aqueous special dyes can be added to enhance gross visualization of the vascular system. Alternatively, gadolinium or other aqueous contrast agent can be added to improve visualization during MRI or other advanced imaging modalities.
  5. The mixture should have no visible solid material and easily pass through a 30 gauge needle. FIG. 2 is a CT picture of a grey parrot that has been filled with this composition. The complete vascular system of the parrot is noted to be uniformly filled with the radiopaque composition.

Example 2

The process of Example 1 is repeated with a gelatin capsule loaded with barium sulfate and gelatin in like amounts. With the placement of the capsule into water and upon dissolution as detailed above, the resulting gelatin solution achieves identical results to Example 1.

Example 3

The process of Example 1 is repeated with a flush of solution of 10% neutral buffered formalin in place of the isotonic solution. The formalin solution made from: Sodium phosphate, monobasic 4.0 gm; Sodium phosphate, dibasic 6.5 gm; Formaldehyde, 37% 100.0 ml; Distilled water 900.0 ml. The resulting animal tissue is fixed and well suited for vivisection after scanning.

The foregoing description is illustrative of particular embodiments of the invention, but is not meant to be a limitation upon the practice thereof. The following claims, including all equivalents thereof, are intended to define the scope of the invention.

The invention claimed is:
1. A process of preparing for imaging a vascular system of a subject having capillaries comprising:
  placing a live subject under anesthesia or sedation;
  placing and securing a first intravenous (IV) catheter and a second IV catheter at opposite ends of a vessel in the body of said subject;
  ligating or occluding a section of said vessel between said first IV catheter and said second IV catheter;
  flushing isotonic fluid through the vascular system in an amount to 20-60 total weight percent of a body of the subject to produce clear to weak blood tinged fluid exiting said second IV catheter;

infusing a radiopaque composition comprising: an opacifying agent having a size of less than 10 microns; an aqueous gelatinous substance present from 5 to 20 percent weight by volume into said first IV catheter at a temperature of 45 to 90 degrees Celsius until said subject is fully perfused with said radiopaque composition; and waiting a time interval for said radiopaque composition to cool and form a solid gel to uniformly fill the capillaries as part of fill of the complete vascular system.

2. The process of claim 1 wherein said inorganic opacifying agent is present in from 10 to 25 percent weight by volume.

3. The process of claim 1 wherein said inorganic opacifying agent is barium sulfate or barium titanate.

4. The process of claim 3 further comprising an inorganic metal salt soluble in said aqueous solvent.

5. The process of claim 4 wherein said inorganic metal salt is at least one of aluminum trihydroxide, bismuth iodide, silver nitrate.

6. The process of claim 1 wherein said inorganic opacifying agent is stainless iron oxide, zinc oxide, elemental iodine, or a combination thereof.

7. The process of claim 1 wherein said an inorganic opacifying agent has median particle size of from 5 nanometers to 10 microns.

8. The process of claim 1 further comprising a dye.

9. The process of claim 1 wherein said aqueous solvent is isotonic.

10. The process of claim 1 wherein said aqueous solvent further comprises a water miscible co-solvent of formalin, $C_1$-$C_4$ alkyl alcohol, acetone, phenol, or a combination thereof.

11. The process of claim 1 wherein said subject is one of: a bird, a reptile, a mammal, or a fish.

12. The process of claim 1 further comprising performing an imaging scan on the subject.

13. The process of claim 1 wherein the temperature is between 45 and 60 Celsius.

14. A process of preparing for imaging a vascular system of a subject having capillaries comprising:

placing and securing a first intravenous (IV) catheter and a second IV catheter at opposite ends of a vessel in the body of said subject;

ligating or occluding a section of said vessel between said first IV catheter and said second IV catheter;

flushing isotonic fluid through the vascular system in an amount to 20-60 total weight percent of a body of the subject to produce clear to weak blood tinged fluid exiting said second IV catheter;

infusing a radiopaque composition comprising:

an opacifying agent having a size of less than 10 microns that is non-toxic and excludes lead and uranium, and an aqueous gelatinous substance present from 5 to 20 percent weight by volume into said first IV catheter at a temperature of 45 to 90 degrees Celsius until said subject is fully perfused with said radiopaque composition; and waiting a time interval for said radiopaque composition to cool and form a solid gel to uniformly fill the capillaries as part of fill of the complete vascular system.

15. The process of claim 14 wherein said subject is one of: a bird, a reptile, a mammal, a fish, a plant, or a human cadaver.

16. The process of claim 14 further comprising performing an imaging scan on the subject.

17. The process of claim 14 wherein the temperature is between 45 and 60 Celsius.

18. The process of claim 1 wherein the temperature is between 45 and 70 Celsius.

* * * * *